United States Patent [19]

Rogers et al.

[11] 4,006,143
[45] Feb. 1, 1977

[54] HETEROCYCLIC SUBSTITUTED PYRIMIDINE COMPOUNDS

[75] Inventors: Edward F. Rogers, Middletown; John Hannah, Matawan, both of N.J.; Richard A. Dybas, Center Square, Pa.

[73] Assignee: Merck & Co., Inc., Rahway, N.J.

[22] Filed: Oct. 16, 1975

[21] Appl. No.: 623,211

Related U.S. Application Data

[63] Continuation-in-part of Ser. No. 459,501, April 9, 1974, abandoned, which is a continuation-in-part of Ser. No. 224,620, Feb. 8, 1972, abandoned.

[52] U.S. Cl. .................. 260/256.4 N; 260/2.1 R; 260/256.5 R; 424/251
[51] Int. Cl.[2] .................................. C07D 401/14
[58] Field of Search ............ 260/256.4 W, 256.5 R

[56] References Cited

UNITED STATES PATENTS

| | | | |
|---|---|---|---|
| 3,030,364 | 4/1962 | Rogers et al. | 260/256.4 N |
| 3,030,365 | 4/1962 | Rogers et al. | 260/256.4 N |
| 3,155,572 | 11/1964 | Rogers et al. | 260/256.4 N |
| 3,385,857 | 5/1968 | Mizzoni et al. | 260/256.4 N |
| 3,920,651 | 11/1975 | Ecsery et al. | 260/256.4 N |

*Primary Examiner*—Donald G. Daus
*Assistant Examiner*—James H. Turnipseed
*Attorney, Agent, or Firm*—Walter Patton; Richard A. Thompson; J. Jerome Behan

[57] ABSTRACT

Novel compounds of the following formula:

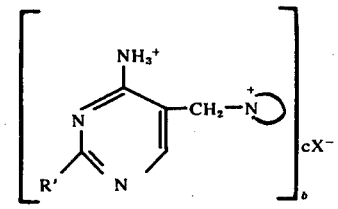

wherein R' is alkyl of 1 to 3 carbon atoms, $X^-$ is a nontoxic anion; $b$ and $c$ are positive numbers having values such that the positive charge of $b$ moles of cation are neutralized by $c$ moles of anion $X^-$; and $-N\rangle$ is a bicyclic heterocyclic base, of the group consisting of:

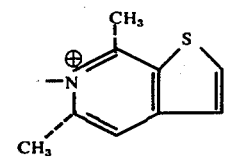

A

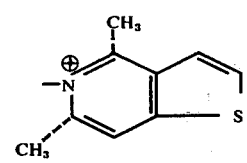

B and

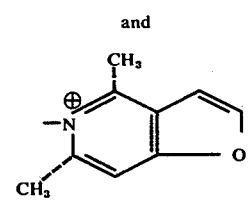

C wherein the dotted line indicates that the methyl group can be present or a hydrogen group can be present, with the proviso that the two alpha methyl groups are not present at the same time, but that one alpha methyl group is required. These compounds have superior coccidiostatic activity.

9 Claims, No Drawings

HETEROCYCLIC SUBSTITUTED PYRIMIDINE COMPOUNDS

This application is a continuation-in-part of co-pending application U.S. Ser. No. 459,501 filed Apr. 9, 1974, now abandoned which in turn is a continuation-in-part of co-pending application U.S. Ser. No. 224,620 filed Feb. 8, 1972, now abandoned.

This invention relates to novel heterocyclic-substituted pyrimidine compounds useful in the prevention and cure of coccidiosis. The novel compounds are effective in controlling coccidiosis when fed in relatively small amounts to poultry or other animals.

Coccidiosis is a common and widespread poultry disease caused by several species of protozoan parasites of the genus Eimeria, such as *E. tenella, E. necatrix, E. acervulina, E. maxima, E. hagani* and *E. brunetti. E. tenella* is the causative agent of a severe and often fatal infection of the ceca of chickens which is manifested by extensive hemorrhage, accumulation of blood in the ceca, and the passage of blood in the droppings. *E. necatrix* as well as certain other species attack the small intestine of the chick causing what is known as intestinal coccidiosis. Related species of coccidia such as *E. melagridis* and *E. adenoides* are causative organisms of coccidiosis in turkeys. When left untreated, the severe forms of coccidiosis lead to poor weight gain, reduced feed efficiency and high mortality in fowl. The elimination or control of coccidiosis is, therefore, of paramount importance in the poultry-raising industry.

It has now been found that certain pyrimidine compounds are highly active against the protozoa responsible for coccidiosis, including protozoa which are resistant to known coccidiostats. One object of this invention is to provide such compounds. Another object is to provide syntheses of such substances. A further object is the provision of animal feeds and feed supplements and of water soluble compositions containing these pyrimidine compounds. Other objects will be apparent from the following discussion of our invention.

According to this invention, it has been found that certain 5-methyl(heterocyclic)-2-loweralkyl-4-aminopyrimidine compounds, wherein the heterocyclic substituent is substituted with at least one methyl group, are very effective in preventing and treating coccidiosis. They are particularly valuable in the cure and control of diseases caused by various "resistant" strains of Eimeria. The term "resistant" is one that is applied to field strains of parasites which do not appear to be controlled by some commercially available coccidiostats. These parasites appear identical to known species, yet are presumed variants insofar as their susceptibility to the commercial coccidiostats is concerned. The novel compounds of this invention, besides being effective coccidiostats against various species, also control one or more of the "resistant" species.

The compounds of this invention have the following formula:

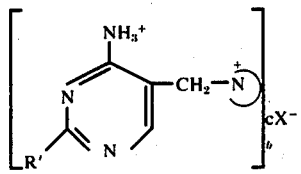

wherein R' is alkyl having one to three carbon atoms; X⁻ is a nontoxic anion; b and c are positive numbers such that the positive charge of b moles of cation are neutralized by c moles of anion X⁻; and -N͡ is a bicyclic heterocycle base, of the group consisting of:

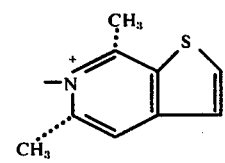

A

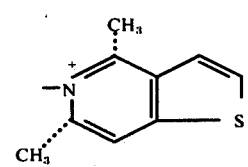

B and

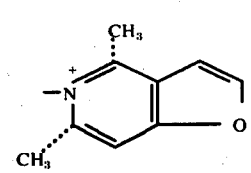

C wherein the dotted line indicates that the alpha methyl group can be present or a hydrogen group can be present with the proviso that one and only one methyl group is present.

As described more fully below, these anticoccidial compounds are prepared by reaction of 2-R'-4-amino-5-halomethyl-pyrimidine or 2-R'-4-amino-5-alkoxymethyl pyrimidine with the bicyclic heterocyclic base.

It will be apparent to one skilled in the art that other position isomers and homologues of the above compounds can be easily prepared and possess coccidiostatic activity. Specifically, in the bicyclic ring systems described, there can be up to two methyl substituents, one of which is alpha to the linking nitrogen and the other in any other available position, so long as it is not in the other alpha position. Two illustrations of these compounds are, e.g.:

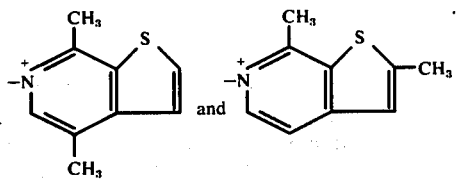

It will be apparent to one skilled in the art that the compounds of the above structural formulas are all most easily synthesized, recovered, and employed as quaternary halide hydrohalide salts wherein the halide can be chloride or bromide.

The preferred compounds of the invention are compounds in which the nitrogen-containing heterocyclic base is thieno[2,3-c]pyridine; thieno[3,2-c]pyridine; or furo[3,2-c]pyridine; respectively:

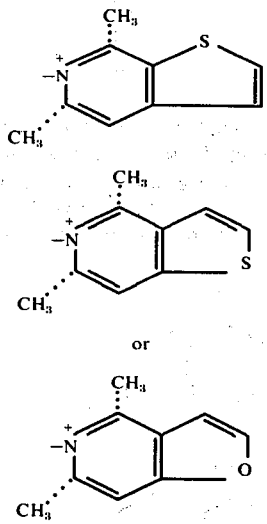

The dotted line indicates that the methyl group can be in either position, or neither, but not in both at the same time. More specifically, 6-[(4-amino-2-ethyl-5-pyrimidinyl)-methyl]-7-methylthieno[2,3-c]pyridinium chloride hydrochloride; 6-[(4-amino-2-ethyl-5-pyrimidinyl)methyl]-2,7-dimethylthieno[2,3-c]pyridinium chloride hydrochloride; 6-[(4-amino-2-ethyl-5-pyrimidinyl)-methyl]-5-methylthieno-[2,3-c]pyridinium bromide hydrobromide; 5-[(4-amino-2-ethyl-5-pyrimidinyl)-methyl]-4-methylthieno[3,2-c]pyridinium chloride hydrochloride; 5-[(4-amino-2-isopropyl-5-pyrimidinyl)-methyl]-6-methylthieno[3,2-c]pyridinium bromide hydrobromide; 5-[(4-amino-2-ethyl-5-pyrimidinyl)-methyl]-4-methylfurano[3,2-c]pyridinium bromide hydrobromide; and 5-[(4-amino-2-ethyl-5-pyrimidinyl)-methyl]-6-methyl-furano[3,2-c]pyridinium chloride hydrochloride are among the most preferred compounds of the above group.

The most preferred salt compounds are the chloride hydrochloride forms. The bromide hydrobromide salts are also preferred. In these preferred compounds, X⁻ is bromide or chloride. The quaternary nontoxic anion can also be any inorganic anion such as iodide or nitrate, sulfate, phosphate, and the like, or the anion of an organic acid such as citric, tartaric, acetic, stearic, succinic, benzoic, phthalic, phenoxyacetic, embonic, abietic, 2-naphthalene sulfonic acid, pamoic acid or 1,5-naphthalene disulfonic acid. It may also be the anion of a polymer such as a polyphosphate or polystyrene-sulfonate ion. The nature of the nontoxic anion is not critical and any anion may be employed as long as it is not unduly toxic for the poultry.

There are a number of processes which can be used to synthesize the group of compounds described in this application. Generally, the appropriately substituted pyrimidine (hereinafter called "the pyrimidine") and the methylated nitrogen-containing bicyclic (hereinafter called "the base"), are condensed by reacting the two in a solvent system. The starting materials, respectively the pyrimidine and the base, are either known and described in the art or can be easily synthesized using processes described in the art.

A. The Acid Ester Process

The preferred process utilizes the appropriate 5-hydroxymethyl pyrimidine which has been converted to the ester of a strong acid in the reaction with the base. By the term, strong acid ester, we mean that the ester at position 5 of the pyrimidine which is formed from the hydroxymethyl group and a strong inorganic acid such as a hydrohalic acid. For example, the 2-R'-4-amino-5-halomethyl pyrimidine dihydrohalide, in which the halogen is bromine or chlorine and R' is as defined above, is reacted directly with the base.

An excess of the base or, alternatively, organic solvents inert under the reaction conditions such as acetonitrile or an N,N-diloweralkyl alkanoamide such as DMF may be employed as the reaction medium. The reaction temperature is not critical and it is preferred to carry out the process at about room temperature. After a short time, the product, which is usually the quaternary salt, crystallizes and is recovered by known techniques such as filtration or centrifugation. This process may be represented as follows:

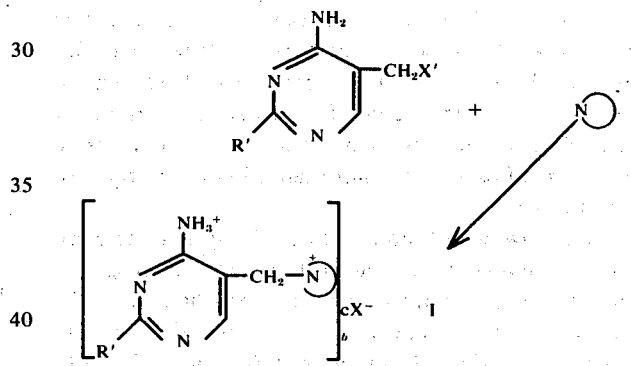

where R' is alkyl of 1 to 3 carbon atoms; X' is a halogen such as chlorine or bromine; X⁻, b, and c are as defined above; and N⃝ is the bicyclic base as defined above.

Although the 5-halomethyl pyrimidines are generally most conveniently employed for reaction with the nitrogen-containing heterocyclic base, the quaternization may also be brought about with other esters of the 2-R'-4-amino-5-hydroxymethyl pyrimidine. Suitable esters are those of organic sulfinic and sulfonic acids such as the methylsulfinate or p-toluenesulfonate. The reaction can be conducted so that the particular salt desired for treating coccidiosis is obtained directly. Alternatively, the quaternary salt recovered from the synthetic reaction medium may be conveniently metathesized to another salt by techniques known in the art.

B. The Ether Cleavage Process

Another process utilizes 2-R'-4-amino-5-methylether pyrimidine in reaction with the base in the presence of an excess of hydrohalic acid, wherein the halogen is chlorine or bromine.

This process can be represented structurally as:

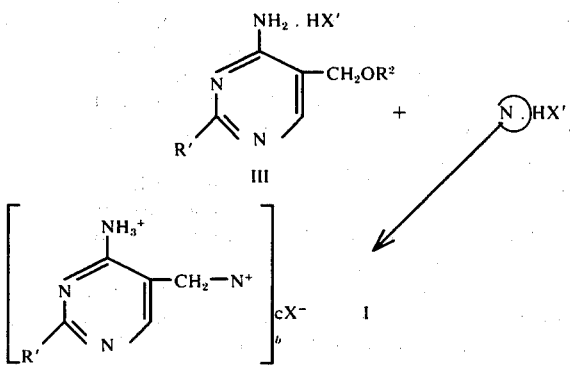

wherein R' is alkyl of 1 to 3 carbon atoms; $R^2$ is an alkyl or aralkyl radical having less than nine carbon atoms; X' is a halogen such as chlorine or bromine; and -N⟩ is as defined above.

The pyrimidine reactant employed (in Formula III above) is the hydrohalide salt of 2-R'-4-amino-5-hydrocarbonoxymethyl pyrimidine. The hydrocarbon radical which forms part of the ether substituent at the 5-position ($R^2$ of Formula III) may be an alkyl or an aralkyl radical, preferably a radical containing less than nine carbon atoms. Thus $R^2$ may be a loweralkyl group such as methyl, ethyl, isopropyl, propyl, t-butyl, or amyl, or benzyl. Pyrimidines having a methoxymethyl or isopropoxymethyl are preferred. These compounds are generally known; those which have not been specifically disclosed are readily prepared by the methods utilized for the known related compounds. For example, see J.A.C.S. 59, 1052 (1947) or U.S. Pat. Nos. 3,161,642 or 2,350,265.

The base employed is also in the form of the hydrohalide salt. These pyrimidinyl methylethers are reacted with the base, the latter as defined above, under the following reaction conditions.

An excess of the base is employed over the pyrimidine. Satisfactory results are obtained when from 1.5 to 10 moles of base are used per mole of pyrimidine.

As will be noted from the above flow diagram, in our process, a pyrimidylmethyl ether (III) is cleaved by the base hydrochloride with formation of the desired quaternary salt. Although the two reactants may be mixed as hydrochloride salts and the reaction carried out as described hereinbelow, it is also possible to charge the pyrimidine and the base to the reaction mixture as free bases, and to form the salts in situ by addition of hydrogen chloride to the reaction mixture.

One feature of this process is that the cleavage of the 2-loweralkyl-4-amino-5-hydrocarbonoxymethyl pyrimidine with the base hydrochloride is brought about in the presence of excess hydrogen halide, i.e., an excess over the amount required to convert all of the pyrimidine and base present to the corresponding hydrohalides. We employ a 7.5 to 100% excess of acid (over the amount required for salt formation).

The process is carried out at atmospheric pressure and at elevated temperatures of between about 110° C. and 200° C. It will be appreciated that the optimum reaction time is dependent to a large degree on the temperature employed. Satisfactory results are obtained in as little as 5 to 10 minutes at higher temperatures whereas 10 to 12 hours or longer may be required at the lower temperatures. When the process is conducted within the preferred temperature range, the quaternary salt is formed in high yield in from about 1 to 8 hours. The reaction mixture is a heterogenous one at several stages of the process so that the efficiency of mixing may become a factor in large-size equipment, and the optimum reaction time will increase as stirring efficiency decreases.

This process is carried out in an organic solvent medium. A number of aromatic and aliphatic solvents can be employed, representative examples of which are toluene, xylene, secondary butyl benzene, tetrachloroethane, tetrachloroethylene and the chlorobenzenes. It is convenient to use a solvent having a boiling point close to the desired reaction temperature so that the process may be conducted under reflux. The solvent should, of course, have a boiling point of at least 110° C. in order to satisfy the temperature conditions discussed above. In addition, the solvent should be water-immiscible for the reason that undesired reaction by-products such as lower alkanols and/or water should be continuously removed from the reaction site in order to achieve optimum yields. Several methods or techniques are suitable for removal of low-boiling byproducts, such as continuous distillation of the organic solvent and replacement thereof by fresh solvent, distillation or refluxing through a steam-cooled condenser which permits escape of low-boiling material but returns the organic solvent to the reaction vessel, or use of commercially-available mechanical separators.

At the end of the reaction period, the product is conveniently recovered by cooling the reaction medium and separating the substantially pure solid from the organic solvent. The product is freed of residual reaction solvent by washing with suitable solvents such as acetonitrile, isopropanol or ether. When this process is carried out under the previously described reaction conditions, the desired products are obtained in yields exceeding 80% and in many cases the yields will approach 90% of theoretical.

C. Other Processes

Other modifications of the two above processes are possible.

For instance, either the 5-hydrocarbonoxymethyl pyrimidine or the 5-hydrocarbonoxymethyl pyrimidine hydrohalide can be reacted with an excess of the base hydrohalide in the absence of a solvent by refluxing at an elevated temperature, preferably between 130°–220° C., under pressure if necessary, for a period between 30 minutes and 10 hours. The hydrohalides can be prepared in situ if desired by first placing the pyrimidine and the base in a low-boiling solvent and passing through hydrohalide gas, evaporating the solvent at a temperature below 100° C., and then heating to the reaction temperature. The product in either case can be recovered by dissolving the reaction product mixture in a solvent like ethanol or propanol and then recrystallizing using the usual techniques.

Another modification utilizes the reaction between the 5-hydroxymethyl pyrimidine hydrohalide, preferably formed in situ by reaction of the 5-hydroxymethyl-4-amino-2-R'-pyrimidine with the base hydrohalide in an organic solvent such as benzene, toluene or xylene, at a pH of between 3 and 6.5. Additional aqueous acid is added if necessary. The reaction is carried out at elevated temperatures, such as between 160°–170° C. The crux of this modification is that the solvent system and water are permitted to evaporate from the reaction mixture, the water is removed from the solvent, and the solvent recycled to prevent the ionization of the hydrohalic acid present with concomitant reduction of the corrosive nature of the system.

Other possible modifications of the process involve reacting a 5-hydroxymethyl-4-amino-2-R'-pyrimidine with the base by adding first the 5-hydroxymethyl pyrimidine into a previously prepared reaction medium comprising a mixture of thionylchloride and an N,N-dialkylformamide, then adding the base. The latter can either be the free base or the base hydrohalide. The reactive medium is prepared from stoichiometric quantities of the two components. This medium is kept at low temperatures (from about −5° C. to 10° C.) while the pyrimidine is added; then the mixture is heated and the base added. After addition of the latter, the reaction is kept at reflux for one to two hours, whereupon the mixture is cooled and the product recovered.

In addition, 5-(triloweralkylammonium)methyl-4-amino-2-R'-pyrimidine halide, especially chloride, will metathesize with the base, as will 5-(triloweralkylphosphonium)-methyl-4-amino-2-R'-pyrimidine halide, especially chloride. Another analogous method utilizes the reaction between the tetrachlorozinc complex of 1-(2-R'-4-amino-pyrimidin-5-yl)methyl-base with ammonia.

Another modification is that the reaction of a 5-halomethyl-4-amino-2-R'-pyrimidine with the base is conducted in dimethylsulfoxide at a temperature between 40°–135° C. for 0.5 to 3.0 hours, in the optional presence of an alkali metal halide salt, such as potassium bromide, then an arylsulfonic acid such as p-toluene sulfonic acid is added to the reaction mixture whereupon the mixture is refluxed for a few minutes, then cooled, and the product recovered. This process is obviously very similar to the acid ester process described above and can also be considered a variation of that process.

In using the compounds of the invention in the treatment and prevention of coccidiosis, they are conveniently fed to poultry as a component of the feed of the animals although they may also be given dissolved or suspended in the drinking water. According to one aspect of the invention, novel compositions are provided in which compounds described above are present as an active anticoccidial ingredient. Such compositions comprise the compounds of the invention intimately dispersed in or admixed with an inert carrier or diluent. By an inert carrier is meant one that is nonreactive with respect to the compounds of the invention and that may be administered with safety to the animals. The carrier or diluent is preferably one that is or may be an ingredient of the animal feed.

The novel compositions which are a preferred feature of the invention are the so-called feed supplements in which the active anticoccidial component is present in relatively large amounts and which are suitable for addition to the poultry feed either directly or after an intermediate dilution or blending step. Examples of carriers or diluents suitable for such feed supplement compositions are solid orally ingestible carriers such as distillers' dried grains, corn meal, citrus meal, fermentation residues, ground oyster shells, Attapulgus clay, wheat shorts, molasses solubles, corn cob meal, edible vegetable substances, toasted dehulled soya flour, soybean mill feed, antibiotic mycelia, soya grits, crushed limestone, and the like. The compounds of the invention are intimately dispersed or admixed throughout the solid inert carrier by methods such as grinding, stirring, milling or tumbling. By selecting proper diluents and by altering the ratio of carrier to active anticoccidial component, feed supplement compositions of any desired concentration may be prepared. Formulations containing from about 1% to about 40% by weight, and preferably from about 2–25% by weight of active anticoccidial component are particularly suitable for addition to poultry feeds, and feed supplement compositions containing from about 5–15% by weight of active anticoccidial component are very satisfactory. The active anticoccidial component is normally dispersed or mixed uniformly in the diluent but in some instances may be sorbed on the carrier. The optimal concentration of active anticoccidial component (coccidiostat) in these feed supplements will depend to some extent on the particular compound employed. Since it is convenient for the feed manufacturer to use about one pound of feed supplement for each ton of finished feed, the preferred concentration of any one of our coccidiostats in a feed supplement is partly a function of the level of active ingredient desired in the finished feed.

In addition to being employed alone in the feed mixes, the novel compounds of this invention can be employed in combination with other known coccidiostats. In the latter case, full spectrum coccidiostatic activity can be assured, even against resistant strains. Other coccidiostats such as amprolium, ethopabate, nicarbazin, robenzidene, sulfaquinoxaline, pyrimethamine, alklomide, sulfanitran, clopidol, nitromide, zoalene, roxarsone, arsanilic acid, enquinolate, deconquinate, monensin, nitrophenide, furazolidone, nihydrazone, nitrofurazone, dimethyalium, and clothiamine, etc., among others, may be used in such combinations.

Examples of typical feed supplements containing a pyridinium quaternary salt dispersed in a solid inert carrier are:

| | | lbs. |
|---|---|---|
| A. | | |
| | 6-[(4-amino-2-ethyl-5-pyrimidinyl)-methyl]-7-methylthieno[2,3-c]pyridinium chloride hydrochloride | 6.0 |
| | Wheat standard midlings | 94.0 |
| B. | | |
| | 5-[(4-amino-2-ethyl-5-pyrimidinyl)-methyl]-4-methylthieno[3,2-c]pyridinium chloride hydrochloride | 10.0 |
| | Corn distillers' dried grains | 90.0 |
| C. | | |
| | 5-[(4-amino-2-ethyl-5-pyrimidinyl)-methyl]-6-methylfurano[3,2-c]pyridinium chloride hydrochloride | 20.0 |
| | Corn germ meal | 30.0 |
| | Corn distillers' grains | 50.0 |

These and similar feed supplements are prepared by uniformly mixing the product with the carrier or carriers.

The feed supplements of the type illustrated hereinabove are usually further diluted with materials such as corn meal or soybean meal before being incorporated in the animal feed. This dilution serves to facilitate uniform distribution of the substance in the finished feed. The finished feed is one that contains a sources of fat, protein, carbohydrates, minerals, vitamins and other nutritional factors.

The amount of drug (anticoccidial compound) required for control of coccidiosis in poultry will, of course, vary somewhat with the specific compound or compounds employed. The compounds of Formula 1 above are effective in preventing the disease when administered at levels of less than about 0.05% by weight of the feed. With the preferred compounds of the invention, i.e., the 6-[(4-amino-2-loweralkyl-5-pyrimidinyl)methyl]thieno[2,3-c]pyridinium or 6-[(4-amino-2-loweralkyl-5-pyrimidinyl)methyl]-thieno-[3,2-c]pyridinium salts, good prophylactic results were obtained when from about 0.01% to about 0.05% by weight of the total feed consumed is administered; for most satisfactory results it is preferred that the poultry feed contain between about 0.001% and 0.025% by weight of the anticoccidial compound. When the anticoccidial compounds are to be employed as therapeutic agents, the higher levels are used for relatively short periods of time. Thus, concentrations of about 0.02%–0.05% by weight of the feed may be advantageously administered in treating an established outbreak of coccidiosis. It is desirable to employ the lowest levels that afford fully adequate control of coccidiosis in order to eliminate as far as possible any risk of side effects that might appear on prolonged feeding of the compounds.

Many of the compounds of the invention are desirably or advantageously administered to poultry by way of the drinking water of the birds. This method of treatment is often employed in the therapeutic use of our compounds since poultry with coccidiosis are apt to consume less solid feed than normal birds. The water-soluble compounds may be added directly to the drinking water. Alternatively, water-soluble powders may be prepared, in which the coccidiostat is intimately admixed with a suitable carrier, such as dextrose or sucrose, and these powders added to the drinking water of poultry as necessary. Such water-soluble powders may contain any desired concentration of coccidiostat, and preparations containing from 1%–25% by weight of active component are suitable.

EXAMPLE 1

6-[(4-Amino-2-ethyl-5-pyrimidinyl)methyl]-7-methyl-thieno-[2,3-c]pyridinium chloride hydrochloride 17.8 G. of 4-amino-2-ethyl-5-pyrimidinylmethyl bromide hydrobromide and 8.94 g. of 7-methylthieno[2,3-c]-pyridine are mixed in 50 ml. dry acetonitrile. The reaction mixture is stirred mechanically overnight at room temperature. The colorless precipitate is collected and washed with ether; after recrystallization from methanol-acetone, 16.5 g. (61.5%) are obtained, m.p. 249°–250° C., dec., identified as 6-[(4-amino-2-ethyl-5-pyrimidinyl)-methyl]-7-methylthieno[2,3-c]pyridinium bromide hydrobromide.

The bromide hydrobromide salt is dissolved in 50 ml. concentrated hydrochloric acid and precipitated with 1.5 liters of acetone. This process is carried out four times. A colorless crystalline solid is obtained, 7.85 g. (60%), m.p. 249°–250° C., dec., identified as 6-[(4-amino-2-ethyl-5-pyrimidinyl)methyl]-7-methylthieno-[2,3-c]pyridinium chloride hydrochloride.

The compounds, 6-[(4-amino-2-ethyl-5-pyrimidinyl)-methyl]-5-methylthieno[2,3-c]pyridinium chloride hydrochloride and 6-[(4-amino-2-methyl-5-pyrimidinyl)methyl]-thieno[2,3-c]pyridinium chloride hydrochloride can be prepared following the above reaction, using the reactants 4-amino-2-ethyl-5-pyrimidinyl-methyl bromide hydrobromide with 5-methylthieno[2,3-c]pyridine or 4-amino-2-methyl-5-pyrimidinyl-methyl bromide hydrobromide with thieno[2,3-c]-pyridine, respectively.

EXAMPLE 2

6-[(4-Amino-2-ethyl-5-pyrimidinyl)methyl]-2,7-dimethylthieno[2,3-c]pyridinium bromide hydrobromide 891 Mg. of 2-ethyl-4-amino-5-bromomethyl pyrimidine hydrobromide is dissolved in 5 ml. of dimethylformamide (DMF), 1.95 g. of 2,7-dimethylthieno[2,3-c]-pyridine is added; a precipitate forms immediately. The precipitate is collected, washed with DMF, and discarded. The filtrates are stirred at room temperature overnight, diluted with ether, and the off-white precipitate collected and washed with ether. The solid is dissolved in methanol, hydrogen bromide gas introduced, and the colorless product isolated from methanol-isopropanol. 270 Mg. of product, 6-[(4-amino-2-ethyl-5-pyrimidinyl)methyl]-2,7-dimethylthieno[2,3-c]pyridinium bromide hydrobromide is recovered, m.p. 215°–216° C., dec., 20% yield.

EXAMPLE 3

5-[(4-Amino-2-ethyl-5-pyrimidinyl)methyl]-4-methyl-thieno-[3,2-c]pyridinium chloride hydrochloride 82.5 G. of 4-amino-2-ethyl-5-pyrimidinylmethyl bromide hydrobromide is suspended in 1000 ml. dry acetonitrile. 82.5 g. of 4-methylthieno[3,2-c]pyridine is added and the reaction mixture is stirred over two days at room temperature. The colorless precipitate is collected, washed with ether, and recrystallized from methanol-isopropanol to give a colorless solid, 69.5 g., m.p. 218.5°–220° C., dec. It is recrystallized again from methanol-isopropanol; 52.1 g. (42%), m.p. 229°–230° C., des., and identified as 5-[(4-amino-2-ethyl-5-pyrimidinyl)-methyl]-4-methylthieno[3,2-c]pyridinium bromide hydrobromide.

The bromide salt, above, is then dissolved in 130 ml. concentrated HCl and precipitated with acetone. This procedure is carried out five times. The result is 33.0 g. (33%), m.p. 229°–230° C., dec., of 5-[(4-amino-2-ethyl-5-pyrimidinyl)methyl]-4-methylthieno[3,2-c]-pyridinium chloride hydrochloride.

The other compounds which are prepared according to this invention are listed in Table I. The condensation process used is that described above, in Examples 1 to 3. In each case the 5-bromomethyl pyrimidine and the base are condensed in an inert solvent in approximately equimolar amounts at ambient temperatures (about 25° C.). The reference to "base type" in the Table is to the structures A, B, or C, each of which is more fully discussed infra.

TABLE I

| EXAMPLE | TITLE OF COMPOUND | BASE TYPE | YIELD | MELTING POINT |
|---------|-------------------|-----------|-------|---------------|
| 4 | 6-[(4-amino-2-n-propyl-5-pyrimidinyl)-methyl]-7-methylthieno[2,3-c]pyridinium bromide hydrobromide | A | 44% | 269–270° C. Dec. |
| 5 | 5-[(4-amino-2-ethyl-5-pyrimidinyl)-methyl]-6-methylthieno[3,2-c]pyridinium | B | 72% | 270–271° C. Dec. |

TABLE I-continued

| EXAMPLE | TITLE OF COMPOUND | BASE TYPE | YIELD | MELTING POINT |
|---|---|---|---|---|
| 6 | 5-[(4-amino-2-ethyl-5-pyrimidinyl)-methyl]-thieno[3,2-c]pyridinium bromide HBr | B | 67% | 271-272° C. Dec. |
| 7 | 5-[(4-amino-2-ethyl-5-pyrimidinyl)-methyl]-4-methylfuro[3,2-c]pyridinium bromide hydrobromide | C | 30% | 228-230° C. Dec. |

EXAMPLE 8

6-[(4-Amino-2-ethyl-5-pyrimidinyl)methyl]-7-methyl-thieno-[2,3-c]pyridinium chloride hydrochloride 50 G. of 2-ethyl-4-amino-5-methoxymethyl pyrimidine, 50 g. of 7-methylthieno[2,3-c]pyridine and 500 ml. of xylene are placed in a 2-liter flask equipped with reflux condenser, stirrer, thermometer and gas inlet tube. Hydrogen chloride gas is added to this mixture over 30 minutes at a rate sufficient to add an amount equivalent to 0.2 moles, that of the pyrimidine. The temperature rises to about 67° C. The gas inlet tube is replaced with a distillation unit and the mixture heated at reflux (138° C.) for two hours during which fresh xylene is added to replace the volume of liquid that distills. An additional 25 g. of 7-methylthieno[2,3-c]pyridine are added and the mixture refluxed for 40 minutes. At the end of the reflux period, the reaction mixture is cooled to 65° C., the xylene decanted, and 50 ml. of acetonitrile added to the residue. The resulting mixture is stirred at room temperature for about 12 hours, filtered, and the solid 6-[(4-amino-2-ethyl-5-pyrimidinyl)methyl]-7-methylthieno-[2,3-c]pyridinium chloride hydrochloride thus obtained washed. The product has a m.p. of 249°-250° C., dec.

The above reaction is also carried out using chlorobenzene as the solvent instead of xylene; and the second addition of 7-methylthieno[2,3-c]pyridine is omitted. The same product, 6-[(4-amino-2-ethyl-5-pyrimidinyl)methyl]-7-methylthieno[2,3-c]pyridinium chloride hydrochloride is obtained.

EXAMPLE 9

6-[(4-Amino-2-ethyl-5-pyrimidinyl)methyl]-7-methyl-thieno-[2,3-c]pyridinium pamoate monohydrate To a mixture of 6-[(4-amino-2-ethyl-5-pyrimidinyl)-methyl]-7-methylthieno[2,3-c]pyridinium chloride hydrochloride (7.14 g., 0.02 mole) and pamoic acid disodium salt (8.64 g., 0.02 mole), there is added 100 ml. water. The reaction mixture is heated on the steam bath for five hours. The cooled mixture is filtered and the precipitate is washed with acetone, then ether, and air dried to give the product as an analytically pure solid, 13.30 g. (96%).

Anal. calc'd for $C_{38}H_{32}N_4O_6S.H_2O$: C, 66.07; H, 4.96; N, 8.11; found: C, 65.82; H, 5.32; N, 7.87.

EXAMPLE 10

6-[(4-Amino-3-ethyl-5-pyrimidinyl)methyl]-7-methyl-thieno-[2,3-c]pyridinium 1,5-naphthalene disulfonate monohydrate To a mixture of 6-[(4-amino-2-ethyl-5-pyrimidinyl)-methyl]-7-methylthieno[2,3-c]pyridinium chloride hydrochloride (7.14 g., 0.02 mole) and 1,5-naphthalenedisulfonic acid disodium salt (7.73 g., 0.021 mole), there is added 75 ml. water. The reaction mixture is heated on a steam bath for two hours and then cooled to room temperature. The precipitate is collected by filtration, washed with some fresh water, then acetone, and finally air dried to give the product as a colorless, analytically pure solid, 11.25 g. (95%).

Anal. calc'd for $C_{25}H_{24}N_4O_6S_3.H_2O$: C, 50.83; H, 4.44; N, 9.48; found: C, 50.26; H, 4.47; N, 9.05.

Many other equivalent modifications of the invention would be apparent to those skilled in the art from a reading of the foregoing without a departure from the inventive concept.

What is claimed is:

1. A compound having the following formula:

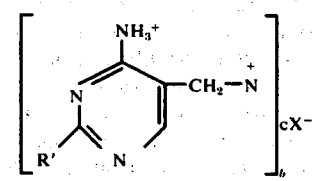

wherein R' is alkyl having 1 to 3 carbon atoms; X⁻ is a nontoxic anion; b and c are integers such that the positive charge of b moles of cation are neutralized by c moles of anion X⁻; and -N⌐ is a member of the group consisting of:

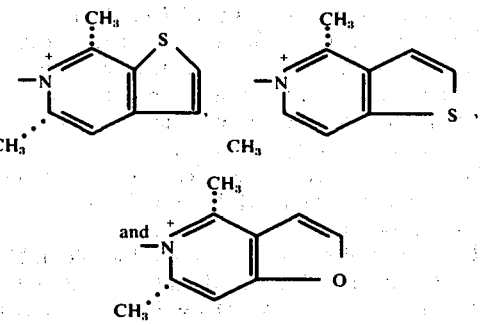

wherein the dotted line indicates that the alpha methyl group can be present or a hydrogen group can be present, with the proviso that one and only one methyl group is present.

2. A compound according to claim 1 wherein the nontoxic anion is chloro or bromo.

3. A compound according to claim 2 wherein R' is ethyl.

4. A compound according to claim 3 wherein -N⌐ is:

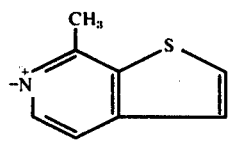

5. A compound according to claim 3 wherein -N⟩ is:

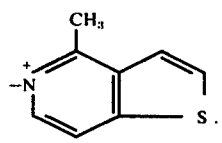

6. A compound according to claim 3 wherein -N⟩ is:

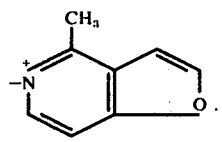

7. A compound according to claim 1 wherein R' is ethyl, X⁻ is chloro and -N⟩ is:

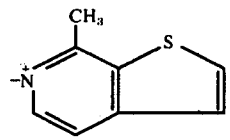

8. A compound according to claim 1 wherein R' is a-propyl, X⁻ is chloro and -N⟩ is:

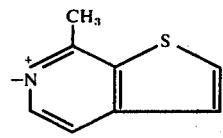

9. A compound according to claim 1 having the following formula:

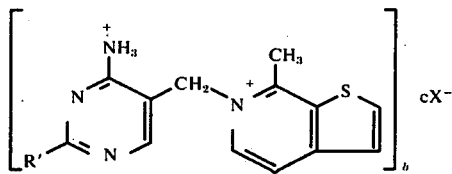

wherein R' is alkyl having 1 to 3 carbon atoms; $X^-$ is a non-toxic anion; $b$ and $c$ are integers such that the positive charge of $b$ moles of cation are neutralized by $c$ moles of anion $X^-$.

* * * * *

UNITED STATES PATENT AND TRADEMARK OFFICE
CERTIFICATE OF CORRECTION

PATENT NO. : 4,006,143
DATED : February 1, 1977
INVENTOR(S) : Edward F. Rogers, John Hannah and Richard A. Dybas It is certified that error appears in the above-identified patent and that said Letters Patent are hereby corrected as shown below:

At Col. 12, line 35 delete the structure:

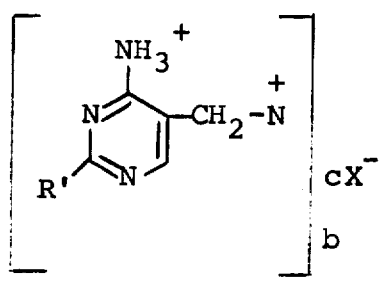

and insert the following structure:

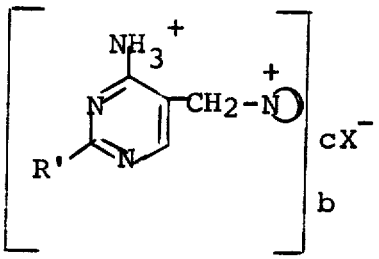

At Col. 12, line 42 delete -N and insert --- -N⃝⁺ ---

UNITED STATES PATENT AND TRADEMARK OFFICE
CERTIFICATE OF CORRECTION

PATENT NO. : 4,006,143
DATED : February 1, 1977
INVENTOR(S) : Edward F. Rogers, John Hannah and Richard A. Dybas It is certified that error appears in the above-identified patent and that said Letters Patent are hereby corrected as shown below:

At Col. 12, line 50 delete second structure and insert the following structure:

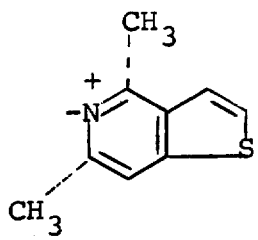

At Col. 12, line 67 delete -N⃝ and insert --- -N⃝⁺ ---.

At Col. 13, line 10 delete -N⃝ and insert --- -N⃝⁺ ---.

At Col. 13, line 21 delete -N⃝ and insert --- -N⃝⁺ ---.

At Col. 14, line 10 delete -N⃝ and insert --- -N⃝⁺ ---.

Signed and Sealed this

Twelfth Day of April 1977

[SEAL]

Attest:

RUTH C. MASON
Attesting Officer

C. MARSHALL DANN
Commissioner of Patents and Trademarks